United States Patent
Scholz et al.

(10) Patent No.: US 6,746,480 B2
(45) Date of Patent: Jun. 8, 2004

(54) FLANGED GRAFT FOR END-TO-SIDE ANASTOMOSIS

(75) Inventors: Hans Scholz, Berlin (DE); Ulf Kruger, Berlin (DE); Utz Settmacher, Berlin (DE)

(73) Assignee: Bard Peripheral Vascular, Inc., Tempe, AZ (US)

( * ) Notice: Subject to any disclaimer, the term of this patent is extended or adjusted under 35 U.S.C. 154(b) by 0 days.

(21) Appl. No.: 09/898,793

(22) Filed: Jul. 3, 2001

(65) Prior Publication Data

US 2001/0041932 A1 Nov. 15, 2001

Related U.S. Application Data

(63) Continuation of application No. 09/125,907, filed as application No. PCT/US96/02714 on Feb. 28, 1996, now Pat. No. 6,273,912.

(51) Int. Cl.[7] .................................................. A61F 2/06
(52) U.S. Cl. ..................... 623/1.31; 623/1.1; 623/1.3; 623/1.35; 623/1.37
(58) Field of Search ................................. 623/1.1, 1.13, 623/1.3, 1.31, 1.32, 1.35, 1.37, 903, 916, 1.49

(56) References Cited

U.S. PATENT DOCUMENTS

| | | | | |
|---|---|---|---|---|
| 3,683,926 A | * | 8/1972 | Suzuki | 128/334 R |
| 3,818,511 A | * | 6/1974 | Goldberg et al. | 3/1 |
| 4,321,914 A | * | 3/1982 | Begovac et al. | 128/1 R |
| 5,156,619 A | * | 10/1992 | Ehrenfeld | 623/1 |
| 5,399,352 A | * | 3/1995 | Hanson | 424/423 |
| 5,456,712 A | * | 10/1995 | Maginot | 623/1 |
| 5,695,504 A | * | 12/1997 | Gifford, III et al. | 606/153 |
| 5,893,886 A | * | 4/1999 | Zegdi et al. | 623/1 |
| 6,019,788 A | * | 2/2000 | Butters et al. | 623/1 |
| 6,136,022 A | * | 10/2000 | Nunez et al. | 623/1.1 |
| 6,187,033 B1 | * | 2/2001 | Schmitt et al. | 623/1 |
| 6,210,430 B1 | * | 4/2001 | Solem | 623/1.11 |
| 6,436,135 B1 | * | 8/2002 | Goldfarb | 623/1.39 |

* cited by examiner

Primary Examiner—Bruce Snow
Assistant Examiner—Cheryl L Miller
(74) Attorney, Agent, or Firm—Morrison & Foerster LLP

(57) ABSTRACT

An inventive flanged graft for end-to-side anastomosis includes a graft with bifurcated flanges. The bifurcated flanges may be symmetrical or asymmetrical relative to one another. The type and size of flange to be used is determined by various factors such as identity of the receiving artery, position of the arteriotomy on the receiving artery, and lumenal diameter of the graft. The graft is preferably anastomosed to the receiving artery using continuous sutures to join the arteriotomy to the peripheral edges of the bifucated flanges. In an alternate embodiment, the inventive bypass graft includes a flared skirt which extends circumferentially about the tubular graft member. The flared skirt has an elliptical shape and is offset from a central longitudinal axis of the graft member.

9 Claims, 2 Drawing Sheets

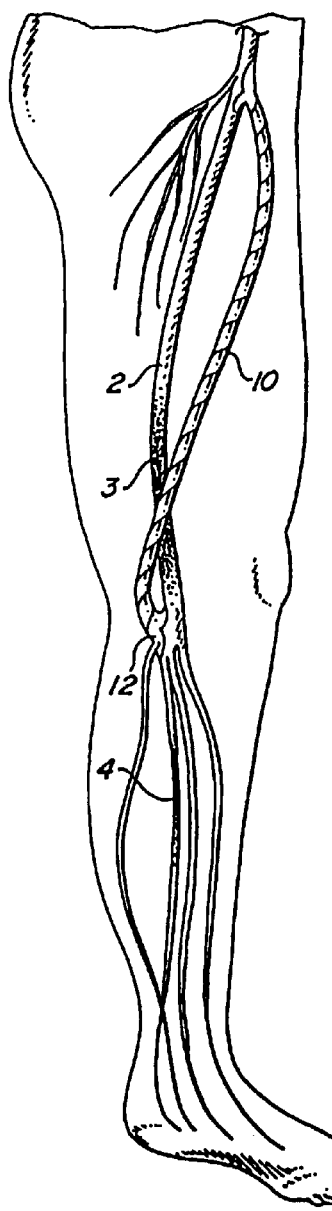
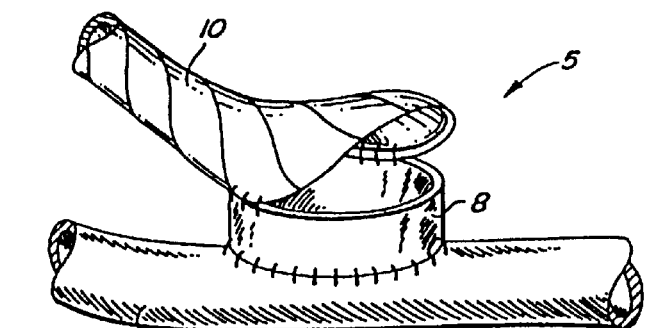
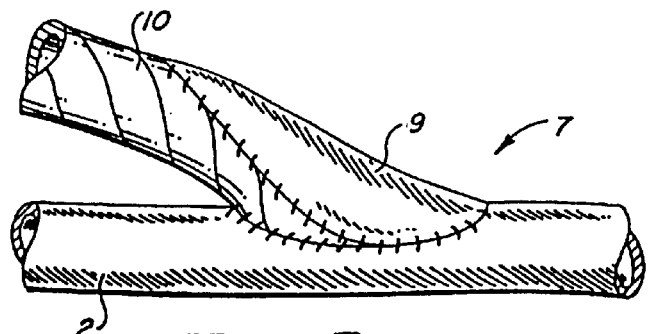
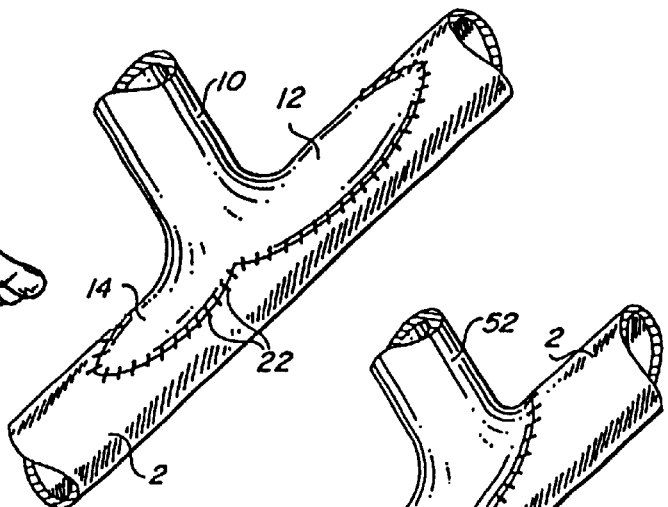
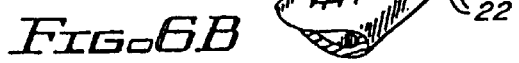

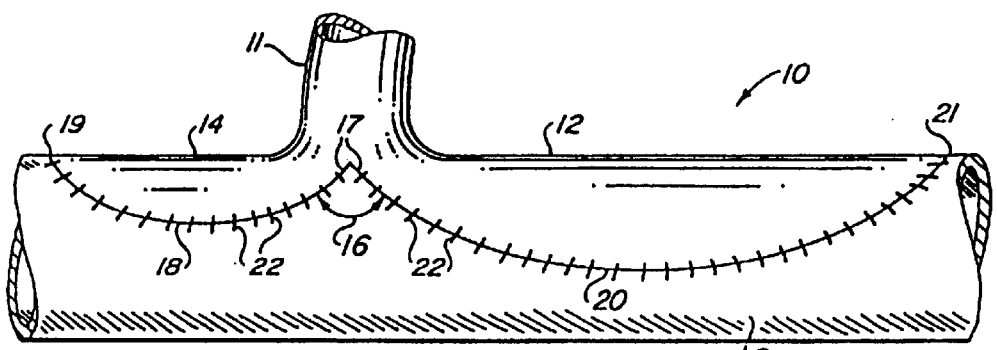
_FIG. 4A_
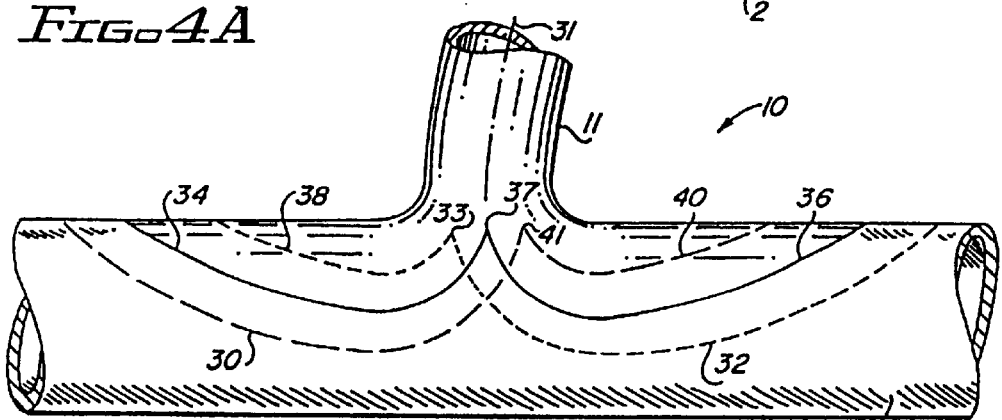
_FIG. 5_
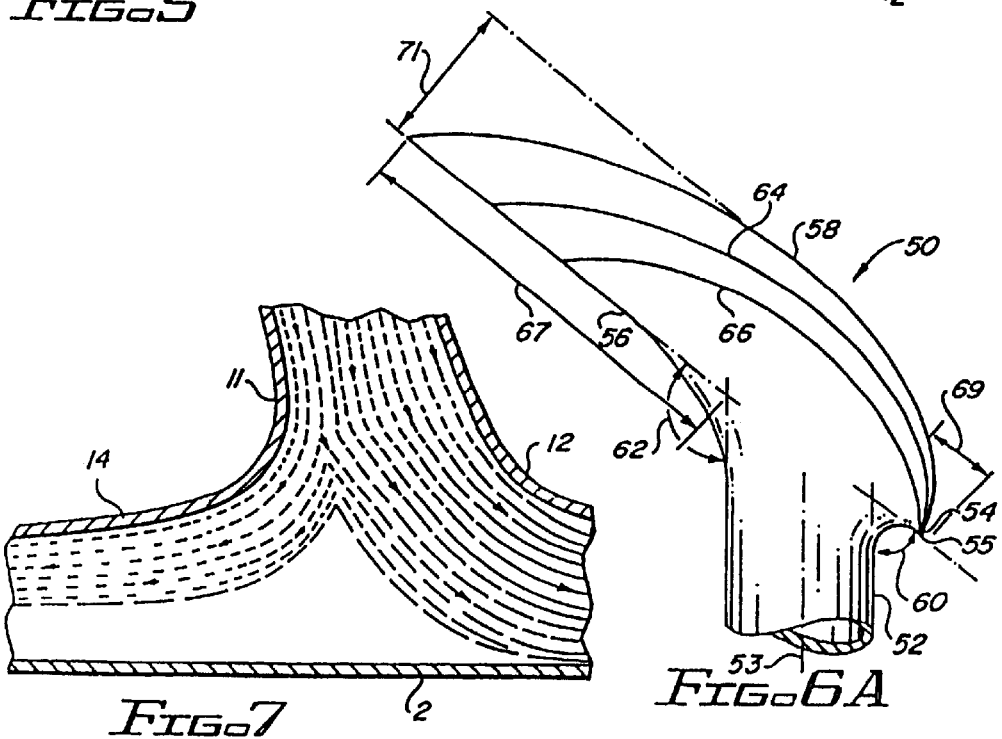
_FIG. 7_     _FIG. 6A_

FLANGED GRAFT FOR END-TO-SIDE ANASTOMOSIS

CROSS-REFERENCE TO RELATED APPLICATION

This application is a continuation of U.S. application Ser. No. 09/125,907, filed as a national stage application from International Application No. PCT/US96/02714, filed Feb. 28, 1996, now U.S. Pat. No. 6,273,912, which is related to U.S. application Ser. No. 09/125,910, now U.S. Pat. No. 6,190,590, the entirety of which is incorporated by reference herein.

BACKGROUND OF THE INVENTION

1. Field of the Invention

The present invention relates generally to vascular grafts, particularly to vascular grafts for end-to-side anastomosis for purposes of bypassing an occluded or diseased section of a blood vessel. More particularly, the present invention is a polytetrafluoroethylene graft having an integral terminal polytetrafluoroethylene flanged cuff section which permits an end-to-side anastomosis with a blood vessel in which the terminal polytetrafluoroethylene flanged cuff section is sutured to the blood vessel and provides a polytetrafluoroethylene-tissue interface between the graft and the blood vessel. The present invention also provides a method and apparatus for forming the flanged polytetrafluoroethylene cuffed section from a tubular polytetrafluoroethylene graft.

2. Description of the Prior Art

The use of cuff grafts for bypassing peripheral vascular occlusive conditions, particularly femoro-crural patch prostheses, is well known in the art. To date, however, either autologous grafts or synthetic grafts with a terminal cuff fashioned from venous tissue at the anastomotic site have been used. Examples of conventional cuffed grafts are the Miller collar described in Miller, J. H., *The Use of the Vein Cuff and PTFE, VASCULAR SURGICAL TECHNIQUES* 2 ed., W. B. Saunders (1989), 276–286 and the Taylor patch described in Taylor, R. S., et al, Improved technique for polytetrafluoroethylene bypass grafting: long-term results using anastomotic vein patches, *Br. J Surg.*, 79:348–354 (1992). Both the Miller graft and the Taylor graft are cuff grafts and each employs a polytetrafluoroethylene graft with an autologous venous cuff at the anastomotic site. The Miller collar and the Taylor patch each use venous tissue at the anastomotic site to avoid a compliance mismatch at the polytetrafluoroethylene-tissue interface.

The present invention offers a new type of anastomosis for femoro-crural bypass in which the graft is fabricated in a flared, double-bulb configuration. The inventive graft configuration offers an optimal geometry for the anastomosis as a function of hemodynamic properties. By optimizing blood flow from the bypass prosthesis to the artery, formation of intimal hyperplasia may be reduced with a concomitant increase in graft patency and decreased morbidity.

The present invention also provides an apparatus and method for forming an integral polytetrafluoroethylene distal flange or cuff on an expanded polytetrafluoroethylene (ePTFE) graft. The apparatus consists of an annular mold having a radially extending annular slot forming an expansion port. The inventive flanged cuff graft is made by first forming an unsintered tubular PTFE vascular graft by extruding a PTFE-lubricant mixture into a billet to form a tubular extrudate, placing the extrudate in the annular mold, and forming an annular cuff by either: 1) application of a negative pressure to the expansion port; or 2) application of positive pressure, as by a highly compliant angioplasty balloon, through the tubular extrudate lumen, to radially displace a section of the tubular extrudate, thereby forming a cuffed graft.

Various different approaches have been taken to fabricate branched grafts. As early as 1938, Bowen, U.S. Pat. No. 2,127,903, discloses a bio-absorbable surgically implantable graft made of animal tissue and a binder formed by wrapping strips of the treated animal tissue about a structural form. U.S. Pat. No. 4,909,979, issued Mar. 20, 1990 to Possis, discloses a method of shaping a human umbilical cord for use as a vascular graft. The method employs a mandrel to support and shape the umbilical cord during forming and curing of the cord. The forming and curing process provides a cord with a blood flow restrictor section. PTFE coatings are provide on the mandrel to facilitate mounting the umbilical cord onto the mandrel. A shaping section of the mandrel is provided with a plurality of vacuum openings in the mandrel. The umbilical cord is treated with ethanol and a vacuum applied until the cord is dehydrated. The cord is then exposed to a curative and fixative solution and a vacuum applied until the umbilical cord is cured substantially airtight and circumferentially compressed and compacted around the mandrel forming section. U.S. Pat. No. 4,354,495, issued Oct. 19, 1982 to Bodicky, discloses a method of connecting a PTFE tube to a hub made of a moldable plastic, e.g., polyurethane, acrylics, polyethylene, polycarbonates, etc. The method involves selectively heating a portion of the PTFE tube to form a bulge or protrusion, then inserting the bulge into a mold and molding the moldable plastic hub about the bulge in the mold. Kaneko et al. (U.S. Pat. No. 4,957,508, issued Sep. 18, 1990), disclose an elastomeric medical tube having proximal and distal ends, outwardly flared. The outward flare of the ends is achieved by forming the inner and outer surfaces of the tube to exhibit inverse elastomeric properties, i.e., the inner surface exhibits a dilating force, while the outer surface exhibits a shrinking force. The tube is made of high molecular weight polymers, particularly, polyvinyl halide, polystyrene, polyolefin series polymers, polyester series condensates, cellulose series high polymers, polyurethane series high polymers, polysulfone series resins, polyamides, etc. along with copolymers or mixtures of these. Noshiki et al. (U.S. Pat. No. 5,387,236, issued Feb. 7, 1995), disclose a vascular prosthesis and method of making a vascular prosthesis by providing a vascular prosthesis substrate made of PTFE or other microporous material, and depositing and capturing within the wall of the prosthesis substrate fragments of biological tissue. The biological tissue fragments may be vascular tissues, connective tissues, fat tissues and muscular tissues and/or vascular endothelial cells, smooth muscle cells and fibroblast cells. The impregnation process is conducted by depositing the cellular material on the inner wall of the graft and applying a pressure differential between the luminal and abluminal wall surfaces to drive the tissue fragments into the microporous matrix of the vascular prosthesis. Berry et al. (U.S. Pat. No. 4,883,453, issued Nov. 28, 1989), disclose an aorto-coronary bypass graft and a method of making the graft. The graft consists of a plate portion and at least one tube portion extending from the plate portion. The graft and plate are disclosed as being made of an electrostatically spun fibrous structure. The graft is adhered to the plate by mounting the graft onto a mandrel, applying adhesive to the surface of the plate surrounding an opening in the plate, passing the mandrel through an opening in the plate until the graft contacts the adhesive. The adhesive is any suitable adhesive for the materials forming the plate and the graft. According to the preferred embodiment described in this reference, the graft preferably has a tapered wall thickness, such that the graft wall thickness adjacent the plate is greater than that distant the plate. Hayashi et al. (U.S. Pat. No. 5,110,526, issued May 5, 1992), disclose a process for producing molded PTFE articles. According to this process, unsintered PTFE extrudates are inserted into a sintering mold. The sintering mold has a diameter slightly larger than the outside diameter of the unsintered PTFE extrudate. Clearance between the outside diameter of the unsintered PTFE extrudate and the inside surface of the sintering mold is on the order of 2% of the diameter of the sintering mold. The extrudate is drawn into the sintering mold via a plug, inserted into the terminal lumen of the extrudate and a wire and take-up reel. The PTFE extrudate is cut to match the length of the sintering mold, and the sintering mold is sealed on the cut extrudate end. The assembly is transferred to a sintering oven, and sintered. During sintering, the extrudate expands in contact with the sintering mold and conforms to the shape of the sintering mold. After cooling, the sintered extrudate contracts away from the sintering mold and assumes an even shape corresponding to the sintering mold. Ely, Jr., et al. (U.S. Pat. No. 3,196,194, issued Jul. 20, 1965), disclose an extrusion process for making FEP-fluorocarbon tubing. The extrusion process consists of screw extruding fluid FEP copolymer through a barrel extruder to form a tubular extrudate, placing the tubular extrudate into a heater, pressurizing the tubular extrudate to radially expand the FEP extrudate, and cooling the expanded extrudate to yield a heat shrinkable tube with memory function to the reduced diameter extrudate. U.S. Pat. No. 4,503,568, issued Mar. 12, 1985 to Madras, discloses an arterial bypass prosthesis for end-to-side anastomosis and reduction of anastomotic hyperplasia. The arterial bypass prosthesis consists generally of a connector element including a tubular entrance member, a tubular exit member and a heel member. The tubular entrance receives and provides an entrance passage for blood flow. The tubular exit member is coupled to and angularly offset from the tubular entrance and provides a passage for the blood from the entrance member. The heel member extends substantially coaxially from the exit member. The distal end of the heel member is inserted through the open arteriotomy and into the portion of the vessel upstream of the arteriotomy. The heel may be solid or may include a passage continuous with the entrance and exist members. A throat portion is located intermediate the tubular entrance and exit members and a circumferential skirt substantially surrounds the throat portion. The skirt heals into the adventital tissue of the blood vessel.

With particular reference to the known method for shaping PTFE materials, the following are cited as examples of the state and scope of the art. U.S. Pat. No. 4,482,516, issued Nov. 13, 1984 discloses a process for producing high strength expanded PTFE products having a coarse microstructure. This is the Bowman, et al. patent, which discloses expansion rates up to 400%/sec. The resulting PTFE microstructure is then defined by a "coarseness" index which purports to consider node size, i.e., height and width and fibril length. Tu et al. (U.S. Pat. No. 5,376,110, issued Dec. 27, 1994), disclose a method of making vascular grafts by collagen cross-linking conducted under the influence of alternating pressure across the graft wall. The alternating pressure aids in cross-linking the collagen fibers. Campbell, et al. (U.S. Pat. No. 4,743,480, issued May 10, 1988), disclose a method for extruding and expanding tubular PTFE products in which a helical groove is machined into the extrusion barrel and/or the mandrel. Extrusion of a tubular PTFE product results in an extrudate having nodes angularly displaced between about 85–15 degrees from the longitudinal axis of the extrudate. Finally, Okita (U.S. Pat. No. 4,234,535, issued Nov. 18, 1980), discloses a process for forming expanded PTFE vascular grafts having fibers of smaller diameter at the inner surface of the tubing and fibers of at least two times diameter at the outer diameter of the tubing. The grafts are produced by a process in which PTFE tubular extrudates are formed, then onto drive and take-up capstans. The capstan drive system conveys the extrudate through a heater set at a temperature above 327° C., then into a vacuum case which causes radial expansion of the extrudate at a temperature above 327° C., then, after radial expansion, the vacuum case is cooled, by introduction of cooled air, to a temperature below sintering temperature thereby fixing the tube at the expanded diameter and in the longitudinal direction by tension from the drive and take-up capstans. This patent also discloses and claims the use of cooling air conveyed through the tube lumen during the radial expansion process. By conveying cooled air through the tube lumen, the temperature at the luminal surface is maintained below the PTFE sintering temperature. In this manner, differing fibril diameters at the luminal and abluminal surfaces are formed.

In current clinical practice, a peripheral anastomosis between a bypass prosthesis and a peripheral artery has been performed by either direct anastomosis, interposition of a venous segment at the anastomotic site, anastomosing the prosthesis with a long venous patch sutured into the artery (Linton Patch), enlargement of the prosthesis within the anastomotic region using a venous patch (Taylor Patch) or interposition of a venous cylinder between the prosthesis and the artery (Miller Collar). In femoro-distal bypass grafting, there is growing evidence that compliance mismatch between the graft and the recipient artery and hemodynamic factors are a major cause of thrombosis and the development of subintimal hyperplasia at the anastomotic site.

SUMMARY OF THE INVENTION

It is a principal object of the present invention to provide a new bypass graft for femoro-distal bypass grafting made of microporous expanded polytetrafluoroethylene (ePTFE).

It is a further object of the present invention to provide a femoro-distal bypass graft made of ePTFE having a distal flange suitable for femoro-crural bypass grafting.

It is a further object of the present invention to provide a femoro-distal bypass graft made of ePTFE having a distal flange suitable for arterio-venous patch (AVP) grafting.

It is a further object of the present invention to provide an apparatus and method for making the new bypass graft for femoro-distal bypass grafting.

It is a still further object of the present invention to provide an apparatus and method for making the new bypass graft for femoro-distal bypass grafting utilizing a tubular mold having an circumferential recess extending radially from the central axis of the tubular mold to form a distal flange on an tubular polytetrafluoroethylene graft.

These and other objects, features and advantages of the present invention will be more apparent to those skilled in the art from the following more detailed description of the preferred embodiments of invention taken with reference to the accompanying drawings.

BRIEF DESCRIPTION OF THE DRAWINGS

FIG. 1 is a diagrammatic representation of peripheral vasculature in a hurnal illustrating an implanted femoro-crural bypass graft.

FIG. 2 is a diagrammatic representation a prior art Miller Cuff.

FIG. 3 is a diagrammatic view of a prior art Taylor Patch.

FIG. 4A is a diagrammatic representation of the inventive bypass graft for femoro-bypass anastomosed to a peripheral artery.

FIG. 4B is a perspective view of the inventive bypass graft for femoro-crural bypass anastomosed to a section of the peripheral vasculature.

FIG. 5 is a diagrammatic representation of alternative configurations of the inventive bypass graft for femoro-crural bypass anastomosed to a peripheral artery.

FIG. 6A is a diagrammatic representation of the inventive bypass graft for AVP bypass.

FIG. 6B is a perspective view of the inventive bypass graft for AVP bypass shown anastomosed to a section of the peripheral vasculature.

FIG. 7 is a diagrammatic representation of the hemodynamic flow profile through the inventive femoro-distal bypass graft.

DETAILED DESCRIPTION OF THE PREFERRED EMBODIMENTS

FIG. 1 illustrates a sequential femoro-posterior tibial bypass with a PTFE graft to an isolate popliteal segment and a distal graft. The use of a PTFE graft 10 bypassing an occluded section 3 of the femoral artery or an occluded section 4 of the popliteal artery to restore distal circulation is well known. As noted above, various cuff and patch techniques have been devised. FIG. 2 illustrates a Miller cuff 5 in which a venous segment, typically 3–4 cm of the saphenous vein, is obtained and sutured to an open arteriotomy in the popliteal or tibial arteries to form a cylindrical collar 8 extending outwardly from the artery 2. The venous segment is fashioned into a collar 8 by opening it longitudinally and anastomosing it to the arteriotomy using a 6/0 or 7/0 prolene suture. The collar 8 is then closed with a 6/0 prolene suture. An ePTFE graft 10 is cut to match the circumference of the collar 8 and then anastomosed to the collar 8 using a continuous 5/0 prolene suture. The Miller cuff 5 is indicated in situations where PTFE is to be anastomosed to tibial arteries, the popliteal artery, or in sequential bypass procedures, e.g., femoro-poplitea-tibial bypass.

FIG. 3 illustrates a Taylor patch 7. In a Taylor patch 7 procedure, a length of vein 5–6 cm long is harvested, typically from an available segment of saphenous vein. The harvested vein is opened longitudinally and trimmed to form a diamond-shaped vein patch 9. A distal end of an ePTFE graft 10 is trimmed to a U-shaped open end and a V-shaped slot along an upper surface of the ePTFE graft 10. The U-shaped open end of the ePTFE graft forms the ePTFE-arterial suture line, while the V-shaped slot is sutured to the venous patch 9. The vein patch 9 is laid along the V-shaped slot in the ePTFE graft 10 and the open arteriotomy in the correct orientation and sutured to both the ePTFE graft 10 and the arteriotomy. The suture line extends from a heel of the graft to the toe of the graft about the arteriotomy to complete the Taylor patch bypass graft.

Graft patency for standard end-to-side ePTFE graft/arterial anastomoses has been reported between 21 and 60% for one year patency and between 14 and 38% for three year patency. One year patency using the Miller collar has been reported at 47% for ePTFE crural grafts, with three year patency being 52%. One year patency using the Taylor patch has been reported at 86%, with three year patency being reported at 61%. Chester, J. F., et al, "Interposition vein patches for vascular reconstruction," *Hospital Update*, February 1993. Direct PTFE to artery anastomosis has been criticized because of mechanical distortion of the artery by the relatively rigid PTFE and formation of intimal hyperplasia between the PTFE and the recipient artery. These two factors have been implicated in the high occlusion rates and low graft patency characteristic of direct PTFE to artery anastomoses. Jamieson, C. W., et al, ed. *Vascular Surgery*, 5th Ed., pp. 330–340 (1994).

The preferred embodiments of the inventive flanged graft are illustrated in FIGS. 4A–6. Illustrated in FIG. 4A is a first embodiment of the inventive flanged graft 10 is a bifurcated double bulb configuration in which an ePTFE tubular graft 11 has a distal bifurcation forming flanges 12 and 14. In a distal end-to-side anastomoses the distal end of the graft 11 is anastomosed to an open arteriotomy formed in the wall of a receiving artery 2. To facilitate the anastomosis, increase compliance matching between the ePTFE graft 11 and the receiving artery 2, and optimize hemodynamic flow from the graft 11 into the receiving artery 2, the bifurcated flanges 12 and 14 project in opposing directions substantially perpendicular to the central longitudinal axis of the graft 11. When the graft 11 is positioned in end-to-side relationship with the receiving artery 2, each of the bifurcated flanges 12 and 14 lie substantially parallel to the longitudinal axis of the receiving artery 2 and extend in the proximal and distal directions relative to the receiving artery 2. The bifurcated flanges 12 and 14 preferably have an elongated bulbous configuration which permits the bifurcated flanges 12 and 14 to be circumferentially positioned substantially co-incident with the curvature of the receiving artery 2 and subtending the open arteriotomy (not shown). Bifurcated flanges 12 and 14 are each preferably formed to have a substantially elliptical shape with outer arcuate peripheral edges 18, 20 terminating in a toe portion 19, 21. A heel region 17 is immediately contiguous with the tubular graft 11 and each of the arcuate peripheral edges 18, 20 of bifurcated flanges 12, 14. The juncture between the peripheral edge 18 of flange 14 and the peripheral edge 20 of flange 12 at the heel region 17 form a crotch angle 16. Crotch angle 16 is preferably between 45 and 180° to maximize the strength of the graft at heel region 17.

The bifurcated flanges 12 and 14 may be symmetrical or asymmetrical relative to one another. The selection of symmetrical or asymmetrical bifurcated flanges 12, 14 is preferably determined by the vascular surgeon based upon the identity of the receiving artery 2, position of the arteriotomy on the receiving artery 2 and lumenal diameter of the graft 11. The graft 11 is preferably anastomosed to the receiving artery 2 using continuous sutures 22 to join the arteriotomy to the peripheral edges 18, 20 of the bifurcated flanges 12, 14, the heel region 17 and the crotch angle 16. FIG. 4B depicts a perspective view of the first embodiment of the inventive graft 10 anastomosed to a receiving artery 2.

FIG. 5 illustrates various sizes and symmetries of the bifurcated flanges at the distal end of a tubular ePTFE graft 11 anastomosed to a receiving artery 2. A first graft has asymmetrical bifurcated flanges 30, 40 in which flange 30 has a greater surface area than flange 40, the flange 30 extending laterally from and circumferentially about the graft 11 a greater extent than flange 40. The crotch angle 41 of the first graft is offset toward the shorter flange 40 relative to the median line 31 of the graft 11. The configuration of the first graft having flanges 30, 40 is well suited to end-to-side anastomoses where the angular orientation between the graft 11 and the receiving artery 2 is oblique on the side of the shorter flange 40 and obtuse on the side of the longer flange 30.

A second graft has substantially symmetrical bifurcated flanges 34, 36, with the crotch angle 37 being substantially co-incident with the median line 31 of the graft 11. Both of flanges 34 and 36 extend substantially identical lengths laterally and in opposite directions relative to the graft 11 and the arcuate peripheral edges of the flanges 34, 36 extend circumferentially about the receiving artery 2 to a substantially equivalent extent. The second graft with symmetrical bifurcated flanges 34, 36 is particularly useful where the angular orientation of the end-to-side anastomosis between the graft 11 and the receiving artery 2 is substantially perpendicular.

The third graft, denoted by asymmetrical bifurcated flanges 38, 32, is substantially a mirror image of the first graft, denoted by asymmetrical bifurcated flanges 30, 40. In this third graft, the flange 32 projects laterally from and extends circumferentially about the graft 11 a greater extent than flange 38. The crotch angle 33 of the third graft is offset toward the shorter flange 38 relative to the median line 31 of the graft 11. The configuration of the third graft, having flanges 38, 32 is well suited to end-to-side anastomoses where the angular orientation between the graft 11 and the receiving artery 2 is acute on the side of the shorter flange 38 and obtuse on the side of the longer flange 32.

In each of the three preferred embodiments of the inventive bifurcated flange bypass graft 10, the bifurcated flanges are preferably made of ePTFE and formed as a continuous, integral, monolithic section of the ePTFE tubular graft 11, without intervening seams or overlap regions. The bifurcated flanges may be formed by any of a variety of methods of forming ePTFE, including molding a section of an ePTFE tube, selective expansion of sections of an ePTFE tube, cutting or trimming sections of an ePTFE tube, such as manual cutting or laser cutting or by using the inventive method described in U.S. Pat. No. 6,190,590, which is hereby incorporated by reference for purposes of illustrating one of many methods of making the inventive graft.

From the foregoing, those skilled in the art will understand that the use of asymmetrical bifurcated flanges on the inventive flanged graft 10 is particularly well suited to end-to-side anastomoses where the longitudinal axis of the inflow graft is positioned at an acute angle relative to the receiving artery 2, with the longer flange 12 being distally-oriented and the shorter flange 14 being proximally oriented relative to the direction of blood flow.

Dimensionally, it is preferable to fabricate each bifurcated flange to a length which is between 1 to 5 times the lumenal diameter of the graft. Thus, for a 5 mm graft, the shorter flange should be no less than 5 mm in length measured from the outer surface of the graft to the furthest point on the toe region of the flange, and the longer flange should be no greater than 25 mm, measured from the outer surface of the graft to the furthest point on the toe region of the flange. Circumferentially, each bifurcated flange should extend no greater than 1 times the lumen diameter of the graft about the receiving artery. Thus, where a graft has a lumenal diameter of 5 mm, the bifurcated flange should extend no further than 5 mm measured from the median line of the graft to a point on the arcuate peripheral edge of the flange which is circumferentially furthest from the median line of the graft. These dimensional constraints have been found to represent optimal parameters for an ePTFE femoro-infragenicular bypass graft which does not use a venous patch or collar at the ePTFE-arterial junction. The configuration of bifurcated flanged graft 10 has been found to have an optimal geometry and a reduced probability of developing subintimal hyperplasia as a cause of graft failure. The inventive bifurcated flanged graft 10 has shown minimal presence of zones of low flow velocity or vortex formation at the anastomotic site and exhibits an optimal hemodynamic flow pattern for an end-to-side anastomosis.

Conventional end-to-side anastomoses exhibit complex hemodynamic flow patterns at the anastomotic junction. Zones of low flow velocity, reversed flow velocity and vortex formation are found in virtually all types of known end-to-side anastomoses. Clearly, detailed hemodynamic measurements are difficult to obtain in vivo. A pulsatile flow model was developed to simulate hemodynamic conditions within the distal end-to-side anastomosis of the inventive femoro-infragenicular bypass graft. A closed flow loop system was made by connecting two reservoirs maintained at systolic and diastolic pressure. A magnetic valve was used to generate a pulsatile flow representative of that in the femoral arteries. A blood-analog fluid (7.5% Dextran by weight in distilled water) was used. To enhance sonographic visualization, the blood-analog fluid was seeded (1 g/L) with 40–120 µl SEPHADEX particles (Pharmacia, Uppsala, Sweden). Flow visualization and velocity field measurements were accomplished by direct dye injection and Doppler color flowometry using real-time ultrasonography (Acuson 128 XP/10) with a 5 MHZ linear array transducer having a Doppler frequency of 3.5 MHZ and an aperture size of 3.8 cm. Doppler color flowometry images were continuously recorded using an S-VHS video camera and an S-VHS high resolution video cassette recorder. Images were obtained at specific intervals within the pulsatile cycle using a peak capture techniques which map peak velocities at each pixel in the frame during successive one second intervals. Flow velocity measurements were detected using ultrasound beams transmitted at an angle of 70° to the face of the transducer in an upstream or downstream direction.

The inventive bifurcated flanged graft 10 was tested against the Linton patch and the Taylor patch using the dye injection and Doppler color flowometry flow visualization techniques under both low and high pulsatile flow rates. In both the Linton patch and the Taylor patch, the velocity profile was skewed toward the outer wall of each graft, independent of flow rates. An impingement of the flow stream on the outer wall produced circumferential flow motions in the high flow situation, while under low flow conditions, a region of flow stagnation was identified at the host vessel outer wall and in line with the inner wall of the graft. This point marked a flow split zone where one flow stream moved in the distal branch and one flow stream moved in the proximal branch of the recipient artery. In the inventive bifurcated flanged graft 10, the area of flow splitting was virtually eliminated. Flow vortexing was observed in the toe and heel regions of the Taylor patch and Linton patch. Minimal vortex formation was observed at the anastomotic site of the inventive bifurcated flanged graft 10. The flow profile through the inventive bifurcated flanged graft 10 is depicted in FIG. 7.

Under Doppler color flowometry, both the Linton patch and the Taylor patch produced the following hemodynamic profiles: 1) flow splitting into reversed vortex flow in the upstream and forward flow in the downstream direction, 2) flow jetting and a non-homogeneous flow pattern downstream of the anastomotic site, and 3) low flow regions with zero flow or reverse flow. The primary location for each of these hemodynamic phenomenon were opposite to the graft inlet and along the inner wall of the artery from the toe of the anastomosis to downstream. Variation of flow patterns with deceleration of flow waveform from systole to diastole resulted in and increase of low flow regions in both the Linton patch and the Taylor patch. None of these hemodynamic phenomena were observed with any degree of statistical significance with the inventive bifurcated flanged graft 10, which exhibited a substantially laminar flow pattern illustrated in FIG. 7.

In a clinical study, 65 infragenicular bypass grafts using the inventive bifurcated flanged graft 10 were performed on 62 patients. In 18 of the patients a temporary extracorporeal bypass was inserted between the proximal and distal anastomotic sites for measurement of blood flow and pressure to calculate the peripheral arterial resistance in each of the upstream and downstream directions. Patency of the inventive grafts was tracked. Prior to the bypass operation, all patients underwent Doppler ultrasonographic ankle artery pressure measurements and arteriography. Graft patency was tracked by clinical examination and Doppler ultrasonographic arterial pressure studies on all patients at three month intervals. The morphology of the anastomosis was examined postoperatively by angiography and at each three month interval with Doppler color flowometry. The one year primary patency rate was 60% which remained constant over the second year of follow up. The one year secondary patency rate was 68% while the second year patency rate fell only to 60%.

Turning now to FIGS. 6A and 6B, there is shown a second preferred embodiment of the inventive bypass graft, referred to for purposes of identification as the arterio-venous patch (AVP) prosthesis 50, The AVP prosthesis 50 consists generally of a tubular ePTFE graft member 52 which has an outwardly flared skirt 56 which extends circumferentially about the tubular ePTFE graft member 52. The flared skirt 56 preferably has a generally elliptical shape and is offset from a central longitudinal axis 53 of the tubular ePTFE graft member 52, such that one focal point of the elliptically shape flared skirt 56 is positioned a greater distance from the central longitudinal axis 53 of the tubular ePTFE graft member 52 than another focal point of the elliptically shaped flared skirt 56. Additionally, the flared skirt 56 resides in a plane 55 which is distally and angularly offset relative to the central longitudinal axis 53 of the tubular ePTFE graft member 52. By being distally and angularly offset relative to the central longitudinal axis 53 of the tubular ePTFE graft member 52, the flared skirt 56 forms a toe angle 62 and a heel angle 60 with the tubular ePTFE graft member 52. In accordance with the preferred embodiments of the AVP prosthesis 50, the toe angle 62 is greater than 90° relative to the central longitudinal axis 53 of the tubular graft member 52, while the heel angle 60 is less than 90° relative to the central longitudinal axis 53 of the tubular graft member 52. In accordance with the preferred embodiments of the present invention, it is preferable that the toe angle 62 be within the range of 95° to 160° relative to the central longitudinal axis 53 of the ePTFE tubular graft member 52, while the heel angle 60 be within the range of 20° to 85° relative to the central longitudinal axis 53 of the ePTFE tubular graft member 52.

Flared skirt 56 has a toe section 67 which projects outwardly from the ePTFE tubular member 52 at toe angle 62. The length of toe section 67 may be predetermined during manufacture, or may be trimmed by a vascular surgeon during the implant procedure to accommodate the open arteriotomy at the anastomotic site. A heel section 69 projects outwardly from the ePTFE tubular member 52 at heel angle 60, and in an opposing direction from the toe section 67. A curved outer peripheral edge 58 of the flared skirt 56 subtends a 180° arc and forms a continuous surface interconnecting toe section 67 and heel section 69. Depending upon the desired length of toe section 67, the length of curved outer peripheral edge 58 and the extension distance 71 which the flared skirt 56 projects in the distal direction relative to the ePTFE tubular member 52 will vary. Phantom lines 64, 66 depict alternative curved outer peripheral edges 64, 66 of the flared skirt 56, each having a common beginning point 54 at heel section 69.

The flared skirt 56 is preferably made of ePTFE and is formed as a continuous, integral, monolithic part of the ePTFE tubular graft member 52, without any intervening seam or overlap. The flared skirt 56 may be formed by any of a variety of methods of forming ePTFE, including molding a section of an ePTFE tube, selective expansion of sections of an ePTFE tube, cutting or trimming sections of an ePTFE tube, such as manual cutting or laser cutting or by using the inventive method described in U.S. Pat. No. 6,190,590, which is hereby incorporated by reference for purposes of illustrating one of many methods of making the inventive graft.

As illustrated in FIG. 6B, the flared skirt 56 assumes a curved configuration in its z-axis to enable a suture anastomosis between the outer peripheral edge 58 and about a circumferential aspect of an artery. The flared skirt 56 should, preferably, extend a distance no greater than the lumenal diameter of the ePTFE tubular graft member 52, measured from an upper surface of the toe region 67 to a point along the outer peripheral edge 58 of the flared skirt 56 which is furthest from the upper surface of the toe region 67.

In accordance with the preferred embodiments of the AVP prosthesis 50, the toe region 67 will have a length greater than that of the heel region 69, with the toe region 67 projecting outwardly from the central longitudinal axis 53 of the tubular ePTFE graft member 52 in the direction of the blood flow. As noted above, the length of toe region 67 is variable, preferably within the range of 5 to 25 mm measured from an outer wall surface of the ePTFE tubular graft member 52 adjacent the toe region 67, to a furthest point on the outer peripheral edge 58 of the toe region 67. It has been found preferable, however, to maintain the length of heel region 69 to a fixed length of approximately 3 mm, measured from the outer wall surface of the ePTFE tubular graft member 52 adjacent the heel region 69, for femoro-distal bypass anastomoses.

While the present invention has been disclosed and described with reference to its preferred embodiments, those skilled in the art will understand and appreciate that modifications in material selection, dimension, and construction may be made without departing from the scope of the present invention, which is limited only by the claims appended hereto.

What is claimed is:

1. A vascular graft suitable for end-to-side anastomosis, comprising:

an expanded polytetrafluoroethylene tubular graft member comprising a smooth luminal surface; and at least one flanged section continuous and integral with said tubular graft member, projecting circumferentially outward from a distal end thereof and being angularly displaced with respect to a central axis of the tubular graft member, wherein said flanged section comprises a skirt member comprising a generally elliptical shape having foci offset with respect to the central axis of the tubular graft member and angularly displaced such that a greater aspect of the elliptical shape projects distally and a smaller aspect of the elliptical shape projects proximally relative to the central axis of the tubular graft member.

2. The vascular graft according to claim 1, wherein the skirt member further comprises a toe section and a heel section, the toe section comprising a greater aspect of the elliptical shape and the heel section comprising a lesser aspect of the elliptical shape.

3. The vascular graft according to claim 2, wherein the skirt member further comprises an arcuate outer peripheral edge which subtends an arc of 180°, forming a continuous surface interconnecting the toe section and the heel section.

4. The vascular graft according to claim 2, wherein the toe section is angularly displaced between 95° to 160° relative to the central axis of the tubular graft member.

5. The vascular graft according to claim 2, wherein the toe section has a length between 5 and 25 mm from an adjacent outer surface of the tubular graft member.

6. The vascular graft according to claim 2, wherein the heel section is angularly displaced between 20° to 85° relative to the central axis of the tubular graft member.

7. The vascular graft according to claim 2, wherein the heel section has a length of approximately 3 mm from an adjacent outer surface of the tubular graft member.

8. A vascular graft suitable for end-to-side anastomosis, comprising:

an expanded polytetrafluoroethylene tubular graft member comprising a smooth luminal surface; and at least one flanged section continuous and integral with said tubular graft member, projecting circumferentially outward from a distal end thereof and being angularly displaced with respect to a central axis of the tubular graft member, wherein said at least one flanged section comprises bifurcated flanges projecting in opposite directions, wherein said bifurcated flanges have a substantially elliptical shape.

9. A vascular graft suitable for end-to-side anastomosis, comprising:

an expanded polytetrafluoroethylene tabular graft member comprising a smooth luminal surface; and at least one flanged section continuous and integral with said tubular graft member, projecting circumferentially outward from a distal end thereof and being angularly displaced with respect to a central axis of the tubular graft member, wherein said at least one flanged section comprises bifurcated flanges projecting in opposite directions, wherein said bifurcated flanges are assymetrical, each having a different surface area.

* * * * *